United States Patent [19]
Bruhn et al.

[11] Patent Number: 6,004,789
[45] Date of Patent: Dec. 21, 1999

[54] PROCESS FOR OBTAINING ACYLOINS, PYRUVATE DECARBOXYLASES SUITABLE THEREFOR AND THEIR PRODUCTION AND DNA SEQUENCE OF THE PDC GENE CODING THEM

[75] Inventors: Heike Bruhn, Munich; Martina Pohl, Aachen; Karin Mesch, Mülheim an der Ruhr; Maria-Regina Kula, Niederzier, all of Germany

[73] Assignee: Forschungszentrum Jülich GmbH, Jülich, Germany

[21] Appl. No.: 08/976,852

[22] Filed: Nov. 24, 1997

Related U.S. Application Data

[63] Continuation-in-part of application No. PCT/DE96/00928, May 22, 1996.

[30] Foreign Application Priority Data

May 26, 1995 [DE] Germany .......................... 195 18 809
Jun. 29, 1995 [DE] Germany .......................... 195 23 269

[51] Int. Cl.⁶ ............................... C12N 9/02; C12P 7/24; C12P 7/22; C07H 21/04
[52] U.S. Cl. ..................... 435/189; 435/132; 435/147; 435/148; 435/155; 435/156; 536/23.2
[58] Field of Search ..................... 435/189, 132, 435/147, 148, 155, 156, 157; 536/23.2

[56] References Cited

PUBLICATIONS

Eur J. Biochem, Dec. 1, 1995, 234(2) P650–5, Germany, XP000607025, Bruhn et al., "The Replacement of Trp392 By Alanine Infulences The Cecarboxylase/Carboligase From Zymomonas mobilis." p. 63.

Eur. J. Biochem, Sep. 1, 1994 224(2) P651–61, Germany, XP000607136, Pohl M. et al, "Reversible Dissociation and Unfolding of Pyruvate Decarboxylase From Zymomonas mobilis", p. 658.

Eur. J. Biochem, 1994, Germany, Candy et al., XP 000607055, Investigation of The Cofactor–Binding Site of Zymomonas mobilis, "Pyruvate Decarboxylase by Site–Directed Mutagenesis".

Crout et al., "Applications of Hydrolytic and Decarboxylating Enzymes in Biotransformations", 1994, vol. 9, pp. 1–30.

*Primary Examiner*—Robert A. Wax
*Assistant Examiner*—Einar Stole
*Attorney, Agent, or Firm*—Klaus J. Bach

[57] ABSTRACT

A process for obtaining a pyruvate decarboxylase by isolation from a producer organism. The pyruvate decarboxylase is capable of forming (R)-(−)-phenylacetylcarbinole (I) in ≧95% enantiomer unit with a product ratio of (I) to 2-hydoxypropiophenone of ≧95%. In addition, the pyruvate decarboxylase has a specific activity with regard to phenylacetylcarbinole formation of >1U/mg. It is the aim of the invention to obtain a pyruvate decarboxylase with improved synthesis capacity concerning the formation of (R)-(−)-phenylacetylcarbinole. The process of the invention developed for this purpose is characterized in that use is made of a producing organism with a gene coding for pyruvate decarboxylase from *Zymomonas mobilis*, in the DNA sequence of which the tryptophane radical coding codon TGG is replaced at position 1174–1176 by a codon which codes for an amino acid radical with a reduced volume ratio.

13 Claims, 3 Drawing Sheets

PROCESS FOR OBTAINING ACYLOINS, PYRUVATE DECARBOXYLASES SUITABLE THEREFOR AND THEIR PRODUCTION AND DNA SEQUENCE OF THE PDC GENE CODING THEM

This is continuation-in-part application of international application PCT/DE96/00928 filed May 22, 1996 and claiming the priority of German applications 195 18 809.8 of May 26, 1995 and 195 23 269.0 of Jun. 29, 1995.

BACKGROUND OF THE INVENTION

The invention relates to a process for obtaining acyloins by enzymatic conversion of α-ketocarbon acid and/or aldehydes in the presence of pyruvate-decarboxylase (PDC) and it comprises a PDC suitable therefor as well as their production and the gene coding them.

Acyloins, or respectively, x-hydroxy ketones are compounds with an optically active C-atom, which play an important rule in the synthesis of relatively complex compounds such as, particularly, the (R)-(-) phenylacetylcarbinol (PAC), which is of great economic interest for the manufacture of ephedrine. Here, the R-enantiomere is of interest which is formed by fermentative conversion of pyruvate in the presence of benzaldehyde by means of *Saccaromyces erevisiae* (DE patent 548439 of 1932).

In this synthesis of PAC by means of yeast cells numerous by-products are formed because of the plurality of enzymes present in the yeast and the cell growth is inhibited by the presence of benzaldehyde.

Also, in this conversion the pyruvate-decarboxylase (PDC) isolated from the yeast yields substantial parts of PAC-isomer 2-hydroxypropiophenons.

Figure 1:
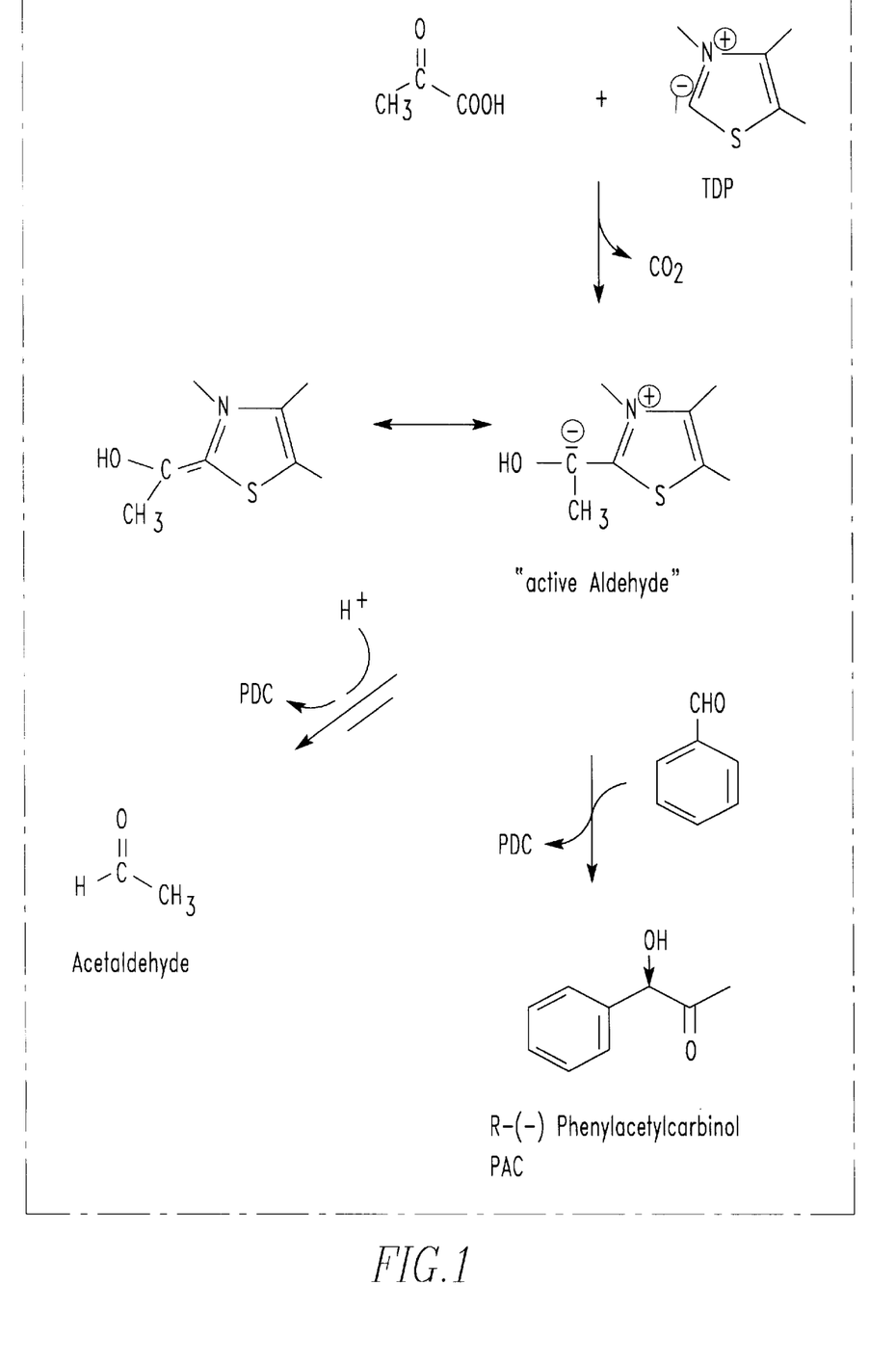
FIG. 1: the reaction chain scheme of the PDC for 30 the example pyruvate and benzaldehyde as substrate and co-substrate with the main path of the decarboxylization and the carboligase side reaction under forming of PAC.

The thiamindiphosphate- and $Mg^{2+}$-dependent PDC (E.C. 4.1.1.1) is very common; it is found in many plants, yeasts and fungi and in some bacteria. It is a catalyst for the non-oxidative decarboxylization of pyruvate to acetaldehyde and, in a side reaction, an acyloin condensation occurs wherein α-hydroxyketones are formed as is apparent from FIG. 1.

Such an enzymatic conversion occurs also on the basis of an aldeyde in place of α-ketonic carbon acid; the aldehyde formed by the decarbooxylization can also participate as "co-substrate" whereby homo acyloins $R-CHOH-CO-R^1$ with R=R' is formed.

Also, the PDC was already isolated from *Zymomonas mobilis*. A comparison of a PDC isolated from yeast with a PDC from *Zymamonas mobilis* with respect to the formation of PAC under comparable conditions however showed a clearly lower capacity of synthesis of the PDC from *Zymomonas mobilis* (S. Bringer-Meyer and H. Sahm, Biocatalysis 1 (1988) p. 321–331).

Surprisingly, it has now been determined that, with a particular gene technological modification of the PDC gene from *Z. mobilis*, a PDC with improved synthesis capacity with respect to the formation of PAC can be obtained which furthermore has a relatively high selectivity for the formation of PAC as compared to 2-hydroxypropiophenone.

The kind of process according to the invention as initially referred to is essentially characterized in that an enzyme is used as a PDC, wherein the tryptophane residue in the substrate canal leading to the active center is replaced by a sterically smaller amino acid residue.

The sterically smaller amino acid residue is particularly a simple, especially an aliphatic amino acid such as, specifically, alanine, glycine, phenylalamine, leucine, isoleucine, arginine or histidine or also serine and threonine.

SUMMARY OF THE INVENTION

A gene-technologically modified new PDC is obtained by an exchange of the codon TGG coding at the location 392 for tryptophane at the location 1174–1176 of the DNA sequence of the PDC-gene of *Z. mobilis* in a manner known per se and by the expression of the PDC in a producer organism such as particularly *E. coli* from which PDC is isolated. The desired mutation occurs for example with the aid of the polymerase chain reaction utilizing the primers given on page 9. The construction of the expression vector pBTac2 for the mutated PDC was performed on the basis of the *E. coli* expression vector pPDC of the wild type enzyme.

The mutated PDC is obtained in a well known manner by chromatographic methods after the cells have been harvested from the raw extract.

By changing the PDC in accordance with the invention, its PAC synthesis capacity is improved by the factor 4. This improvement is the result of the particular weakening or, respectively, elimination of the access limitation in the substrate canal leading to the active center of the enzymes whereby the access tofo the voluminous substrate molecules to the active center and the release of the product formed is facilitated.

A corresponding optimization can generally be achieved with thiamine diphosphate-dependent enzymes which have an access limitation in the substrate canal leading to the active center—either because of a steric nature or because of charge effects: By a corresponding modification of the DNA sequence of the gene coding for the enzyme, that is by the exchange of the codon coding for the access limitation by a codon which codes for an amino acid residue which eliminates the access limitation, the synthesis capacity of the enzyme is substantially increased.

The PDC obtained in this way in accordance with the object of the invention is of great interest for the PAC-synthesis, since, in this way, an optically highly pure R-(−) isomere (>>98%) and a PAC can be obtained which is accompanied by 2-hydroxy-propiophenon only at a low rate (2–3%). The production and isolation of the enzyme from the harvested microorganisms is possible in a relatively simple manner (in comparison to yeast).

With the enzymatic acyloin condensation by means of PDC, linear and/or branched α-ketocarbon acids can be used as substrate and aromatic, cyclic, long-chain or other branched aldehydes can be used as substrate and/or co-substrate. For this purpose, for example, benzaldehyde, cyclohexane aldehyde, furfurol, cinamonaldehyde, krotonealdehyde, pyruvate, 2-ketobutyric acid, 2-ketopentane acid, 2 keto-4-methylhexane acid, 2-keto-4 methyl pentanic acid, 2 keto-4,4-dimethyl-hexane acid, 3-phenyl-2-keto-propane acid may be used.

Further particulars of the invention will become apparent from the subsequent description of detail embodiments described with reference to the accompanying drawings.

DESCRIPTION OF AN EXAMPLE

1. Manufacture of the PDC Mutant PDC-W392A 1.1 Construction of the expression vector pPDC For the expression of the PDC from *Zymomonas mobilis* the vector pBTac2 (Boehringer, Mannheim) was selected. The transcription of the foreign gene is under the control of the strong tac-promoter, a hybrid of trp-and lac UV promoter with the 11-fold or, respectively, 3 fold efficiency of the parental promoters. The operator sequence and the ribosome binding region result from the lacz gene. The regulation of the transcription occurs consequently by the lac—repressor of an over-expressing (laciQ) bacteria strain and can be induced by isopropyl-α-D-thiogalactoside (IPTG). The vector contains a single recognition sequence of the restriction sendonuclease EcoR1, followed by the initiation codon ATG and subsequent additional restriction recognition sequences (sites) so that this vector can be used universally for the expression for gene sequences with and without their own initiation codon.

Figure 2:
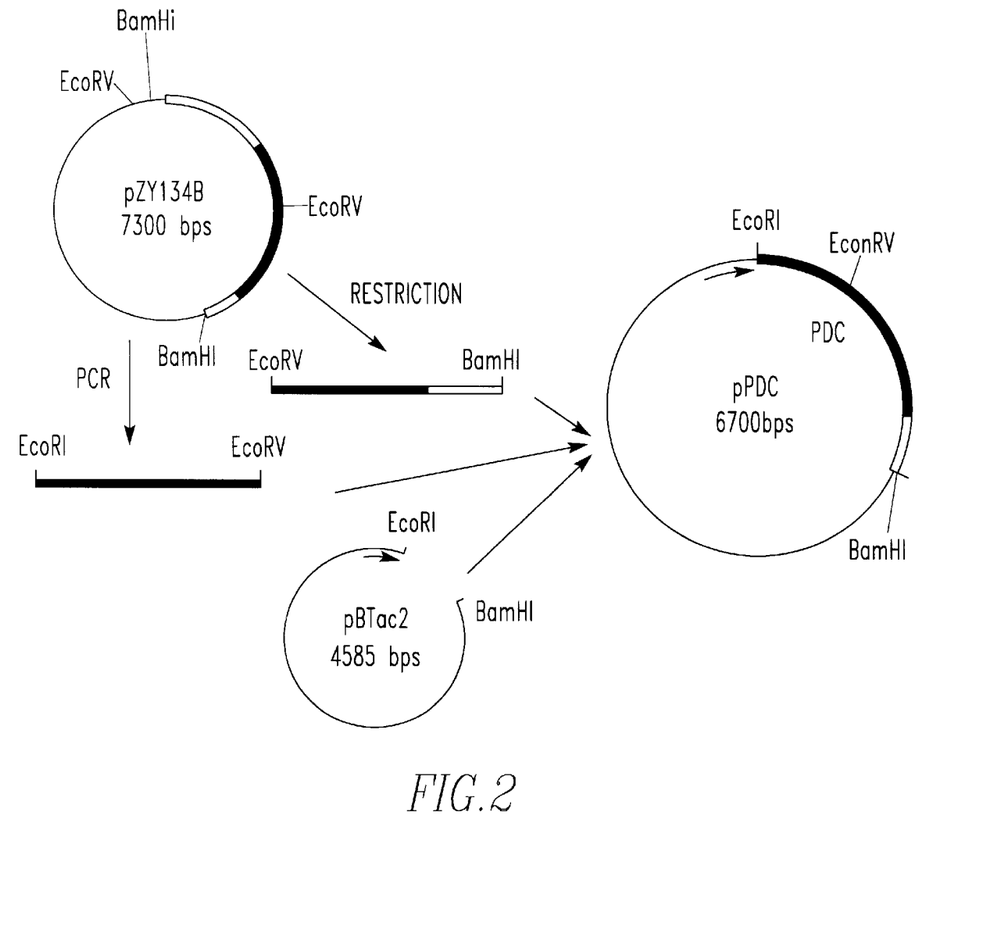
FIG. 2: A construction scheme for the formation of the PDC from *Z. mobilis*-containing expression vectors pPDC.

The strong ribosomal RNA transcription terminators rrnB follow the multiple cloning sites in order to insure the controlled break-off of the transcription. As starting material for the cloning of the PDC genes from *Zymomonas mobilis* (ATCC 29191), the vector pZY134B (G. Sprenger, Institute for biotechnology 2, KFA Jülich) was available. This plasmid contains a 3.2 kB large DNA fragment of *Zymomonas mobilis* with the complete PDG gene inclusive non-coding regions (FIG. 2). In order to facilitate a ligation of the coding sequence into the expression vector, it was necessary to introduce a new restriction recognition sequence in 5'-direction of the imitation codon. The ligation on the gene into the Eco R1-site of the pBTac2-vector insures the optimal distance of the initiation codon of the Shine-Dalgarno sequence of the sector. An elegant and simple method, to modify a DNA sequence, is provided by the polymerase chain reaction (PCR). Repeated cycles of heat denaturization of the DNA double strand and the enzymatic synthesis by a thermo-stable DNA polymerase make the exponential amplification of defined DNA fragments possible. The size and identity of the products are caused by the starting points (primers) of the synthesis. If the primers contain a modification, deletions or additional bases (insertions, those will consequently be present also in the synthetic fragment.

With this method, the required EcoR1-restriction site in the 5'-direction of the initiation codon of the PDC-gene was introduced by connecting during the oligonucleotide synthesis, the recognition sequence of the enzyme at the 5'-end of the primer which complimentary to the gene. Since some endonucleases show a highly reduced activity for the restriction of end position sequences four additional bases were attached up-stream to the EcoRI-site.

The Tag-polymerase mostly used for PCR has no 3'-5'-exonuclease activity (proof-reading). The sequence synthesized by it consequently includes a statistic error rate. Even if this rate can be kept very small at 1/100000 by the selection of suitable reaction conditions, this still requires the sequencing of each fragment in order to insure the integrity of the synthesis. For this reason, not the whole coding region of the PDC gene (1717 bp), but a small fragment (890 bp) from the 5'-terminus up to an individual restriction site (EcoRV) was selected for the amplification (FIG. 2).

The PCR-product was digested with the respective restriction endonucleases EcoR1 and EcoRV.

The missing second part of the PDC gene was obtained by restriction with EcoRV from plasmid pZY134B wherein the fragment (1.2 kb) so generated contains at the 3'-end still an about 350 bp non-translated sequence of the PDC-gene. Both fragments were separated by preparative agarosegelectrophorese, isolated and ligated into the linearized isolated pBTac2(4.6kb). The cloning occurred in *E. coli* JM 109, a strain which over expresses the lac-repressor.

1.2 Molecular Biological Activities

For producing a PDC at the position 392 mutated by tryptophane/alanine exchange, first the codon TGG (tryptophane) present at the wild-type enzyme was exchanged for GCG (alanine) (exchange position 1174–1176 of the gene of the pyruvate-decarboxylase of *Zymomonas mobilis*). A particular imitation was initiated by means of the polymerase chain reaction-supported method described by Ho et al. (S. N. Ho, H. D. Hunt, R. M. Horton, J K Pullen, L. R. Pease, Gene 77 (1989) p. 51).

As a starting point, the PDC gene of *Z. mobilis* in the *E. coli* expression vector pPDC was available (see FIG. 2). The DNA isolation occurred in accordance with standard methods (J. Sambroch, E. F. Fritsch, T. Maniatis, Molecular Cloning (1989), Spring Harbor Laboratory Press).

As a template for the synthesis of the two overlapping individual fragments, the plasmid pPDC was used. The primers (Primer sequences according to attachment) used had a concentration of 0.2–0.4 mM. The reaction was performed with Tag-polymerase (Biomasters, Cologne) in the reaction buffer recommended by the manufacturer with the addition of 1.5 mM $MgCl_2$ and 0.2 mM each of the nucleotide in the "Robocycler" (stratgenes) with the following temperature program: 2.5 minutes 94° C. for the denaturization, then 30 cycles with a 1.5-minute denaturization at 94° C., 1.2 minutes annealing at 48° C. and 2 minutes extension at 72° C. followed by 10 minutes at 72° C. for the completion of the reaction. The annealing temperature varied between 48° C. and 56° C. depending on the theoretical melting point of the primer used. The melting point of the oligonucleotides was calculated on the basis of the following formula:

$$TM=2*(A+T)+3*(C+G)$$

The fragments were separated electrophoretically, isolated, precipitated with ethanol for concentrating them and again retrieved into a tris-HCl buffer, 10 mM, pH 7.4.

In the second combined PCR 50–100 ng of each of the overlapping fragments were utilized as template. The further reaction conditions were the same as in the first reaction. The annealing temperature was selected depending on the melting temperature of the resulting overlapping region of the fragments. The further manipulations (restriction, isolation, ligation) for the replacement of the wild-type DNA in the expression vector pPDC by the mutated fragments occurred in accordance with standard methods (J. Sambrock, E. F. Fritsch, T. Maniatis, Molecular Cloning (1989) Spring Harbor Laboratory Press).

| SEQUENCES OF THE PRIMERS USED |
| --- |

The numbering relates to the 1.(5')-nucleotide of the PDC sequence s = sense, as = antisense.

The mutated bases are underlined

Primer for the synthesis of the 5' individual fragment
- PDC867s
  CTACTCCACCACTGGTTGGACG
- PDC1186AS
  GAGGATTGAAGGAGAGTCACC Primer for the synthesis of the 3'-individual fragment
- PD1159s
  GAAACCGGTGACTCTGCGTTCAATGC
- PBTAC453Aas
  ATCTTCTCTCATCCGCCAAACA (this primer is complementary to the vector sequence at the 3'- end following the PDC-sequence)

Primer for the synthesis of the fusion fragment
- PDC867s
  CTACTCCACCACTGGTTGGAGG
- PBTAC453 as
  ATCTTCTCTATCCGCCAAACA (this primer is complimentary to the vector sequence of the 3'-end following the PDC sequence).

```
ATGAGTTATA CTGTCGGTAC CTATTTAGCG GAGCGGCTTG TCCAGATTGG   50
TCTCAAGCAT CACTTCGCAG TCGCGGGCGA CTACAACCTC GTCCTTCTTG  100
ACAACCTGCT TTTGAACAAA AACATGGAGC AGGTTTATTG CTGTAACGAA  150
CTGAACTGCG GTTTCAGTGC AGAAGGTTAT GCTCGTGCCA AAGGCGCAGC  200
AGCAGCCGTC GTTACCTACA GCGTTGGTGC GCTTTCCGCA TTTGATGCTA  250
TCGGTGGCGC CTATGCAGAA AACCTTCCGG TTATCCTGAT CTCCGGTGCT  300
CCGAACAACA ACGACCACGC TGCTGGTCAT GTGTTGCATC ACGCTCTTGG  350
CAAAACCGAC TATCACTATC AGTTGGAAAT GGCCAAGAAC ATCACGGCCG  400
CCGCTGAAGC GATTTACACC CCGGAAGAAG CTCCGGCTAA AATCGATCAC  450
GTGATCAAAA CTGCTCTTCG CGAGAAGAAG CCGGTTTATC TCGAAATCGC  500
TTGCAACATT GCTTCCATGC CCTGCGCCGC TCCTGGACCG GCAAGTGCAT  550
TGTTCAATGA CGAAGCCAGC GACGAAGCAT CCTTGAATGC AGCGGTTGAC  600
GAAACCCTGA AATTCATCGC CAACCGCGAC AAAGTTGCCG TCCTCGTCGG  650
CAGCAAGCTG CGCGCTGCTG GTGCTGAAGA AGCTGCTGTT AAATTCACCG  700
ACGCTTTGGG CGGTGCAGTG GCTACTATGG CTGCTGCCAA GAGCTTCTTC  750
CCAGAAGAAA ATGCCAATTA CATTGGTACC TCATGGGGCG AAGTCAGCTA  800
TCCGGGCGTT GAAAAGACGA TGAAAGAAGC CGATGCGGTT ATCGCTCTGG  850
CTCCTGTCTT CAACGACTAC TCCACCACTG GTTGGACGGA TATCCCTGAT  900
CCTAAGAAAC TGGTTCTCGC TGAACCGCGT TCTGTCGTTG TCAACGGCAT  950
TCGCTTCCCC AGCGTTCATC TGAAAGACTA TCTGACCCGT TTGGCTCAGA 1000
AAGTTTCCAA GAAAACCGGT TCTTTGGACT TCTTCAAATC CCTCAATGCA 1050
```

-continued

| SEQUENCES OF THE PRIMERS USED | |
|---|---|
| GGTGAACTGA AGAAAGCCGC TCCGGCTGAT CCGAGTGCTC CGTTGGTCAA | 1100 |
| CGCAGAAATC GCCCGTCAGG TCGAAGCTCT TCTGACCCCG AACACGACGG | 1150 |
| TTATTGCTGA AACCGGTGAC TCTTGGTTCA ATGCTCAGCG CATGAAGCTC | 1200 |
| CCGAACGGTG CTCGCGTTGA ATATGAAATG CAGTGGGGTC ACATTGGTTG | 1250 |
| GTCCGTTCCT GCCGCCTTCG GTTATGCCGT CGGTGCTCCG GAACGTCGCA | 1300 |
| ACATCCTCAT GGTTGGTGAT GGTTCCTTCC AGCTGACGGC TCAGGAAGTT | 1350 |
| GCTCAGATGG TTCGCCTGAA ACTGCCGGTT ATCATCTTCT TGATCAATAA | 1400 |
| CTATGGTTAC ACCATCGAAG TTATGATCCA TGATGGTCCG TACAACAACA | 1450 |
| TCAAGAACTG GGATTATGCC GGTCTGATGG AAGTGTTCAA CGGTAACGGT | 1500 |
| GGTTATGACA GCGGTGCTGC TAAAGGCCTG AAGGCTAAAA CCGGTGGCGA | 1550 |
| ACTGGCAGAA GCTATCAAGG TTGCTCTGGC AAACACCGAC GGCCCAACCC | 1600 |
| TGATCGAATG CTTCATCGGT CGTGAAGACT GCACTGAAGA ATTGGTCAAA | 1650 |
| TGGGGTAAGC GCGTTGCTGC CGCCAACAGC CGTAAGCCTG TTAACAAGCT | 1700 |
| CCTCTAG | 1707 |

1.2 Expression and Purification.

By expression of the modified DNA in E. coli cells an enzyme (PDC-W392A) according to the invention was obtained. The mutated enzyme (mutant) was expressed in accordance with the following procedure and was obtained pure out of the cell extract:

The E. coli cells carrying the expression plasmid for the mutant PDC-W392A were fermented for the selection in LB medium including 100 µg/ml ampicillin. The medium was innoculated with precultures in the stationary growth phase at a ratio of 1:50 and incubated at 37° C. and 220 rpm (stirring speed).

The induction of the expression occurred at an OD60 of 0.6 by the addition of 1 mM IPTG. Under these conditions, the PDC-mutant was over-expressed in E. coli with 20% 6 of the soluble protein.

For the production of sufficient amounts of enzyme the expression as described above was performed in an 8 liter fermenting apparatus. A pH value of 7.0 and an air flow of 101/h were adjusted. The stirring speed was 200 rpm. To avoid excessive foam formation, polypropyleneglycol was added as necessary. The cells were harvested after a 3 hour long expression by cooled continuous centrifugation. They were then subjected to grinding using glass beads. For this purpose, a 30% cell suspension in a Mes/KOH-buffer, 50 mM, pH 6.5, inclusive 5mM $MgCl^2$ and 0.1 mM ThDP was prepared and combined with twice the volume of glass beads (d=0.3mm). Depending on the volume to be treated, the treatment was performed in Eppendorf containers in a Retsch mill or ice-cooled in disintegrators S (maximum volume 80 ml). The grinding occurred over 10 minutes with maximum power. The suspension was then centrifuged, the glass beads with the buffer were washed and the combined centrifugates were filtered (1 µm). The purification of the PDC mutants occurred by column chromatography as follows:

1. Anion Exchange Chromatography

The raw extract (about 110 , about 1.0–1.5g protein) was applied to a Q-Sephiarose Fast Flow (Pharmacia) (2.6×9.5 cm) with a flow rate of 5 ml/min using a FPLC apparatus of the company Pharmacia. The enzyme was eluated by applying a linear NaCl-gradient (of 0–200 mM) in 10 mM Mes/KOH, pH 6.5, 2 mM $MgCl_2$, 0.1 mM ThDP, with 100mM NaCl. The fractions containing the target protein were identified by an activity test (see below).

2. Hydrophobic Interaction Chromatography (HIC)

The combined fractions were adjusted to an ammonium sulfate content of 50% saturation by the addition of a volume of saturated ammonium sulfate solution. The hydrophobic interaction chromatography was performed with butyl-sepharose (Pharmacia) column 5*8 cm) with a flow rate of 2 ml/min. Before being charged the material was brought to equilibrium with 40%b ammonium sulfate in 50 mM Mes/KOH, 2mM $MgCl_2$, 0.1 mM ThDP. The enzyme was eluated in the same buffer with a falling ammonium sulfate gradient (40–0%) at 24%. The target fraction was again identified by means of an activity test and combined (ca. 160 ml).

3. Desalting by way of Sephadex G25 and buffer change to 50 mM Mes/KOH, 2 mM $MgCl_2$, 0.1 mM ThDP. The flow rate was 20 ml/min. Subsequently, lyophilization was employed.

1.3 Activity Test (Decarboxylization Reaction)

Determination of the enzymatic activity was performed in a coupled enzymatic test, wherein the NADH oxidation by the auxiliary enzyme alcohol-dehydrogenase of yeast (E.C. 1.1.1.1) is surveyed photometrically. The reaction preparation contained 16.9 mM pyruvate 0.18 mM NADH and 10 U ADH in 50 mM Mes/KOH, pH 6.5, 20 mM $MgSO_4$, 1.5 mM ThDP. An enzyme unit PDC (1 U) corresponds to the enzyme amount which the conversion of 1 µmol substrate catalyzes in one minute at 30° C. The enzyme activity is calculated as follows:

$$C(V/ml) = \frac{\Delta E/min \cdot V}{\varepsilon * d * v} * f$$

$\varepsilon(NADH) = 6.3 \ 1* \ mMol^{-1} * cm^{-1}$
V=total volume
v=probe volume d=layer thickness of the cuvette (1 cm)

ΔE/min—extinction decrease per minute f=dilution factor of the probe

2. Use of PDC-W392A for the PAC synthesis

Chiral acyloins can be produced starting with an α-ketocarbon acid or, respectively, with aldehyde as substrate and another aldehyde as cosubstrate by means of PDC or PDC mutants.

As examples, the following application are named:

PAC Synthesis Starting with Pyruvate and Benzaldehyde

The synthesis preparation contained 40 mM pyruvate, 70 mM benzaldehyde and 10 U/ml PDC-W392A in a Mes/KOH buffer, 50 mM, pH 6.5, 20 mM MgSO$_4$, 1.5 mM ThDP. The reaction was performed for one hour at 37° C. and the PAC formed (6.2 mM) was detected by means of HPLC.

PAC-Synthesis Starting with Acetaldehyde and Benzaldehyde

The PAC synthesis preparation contained 40 mM acetaldehyde in place of pyruvate. Otherwise, the procedure was the same as described above. After one hour, 3.7 mM PAC was formed.

PAC Synthesis with PDC-W392A in a Coupled 3-Enzyme System

Figure 3:
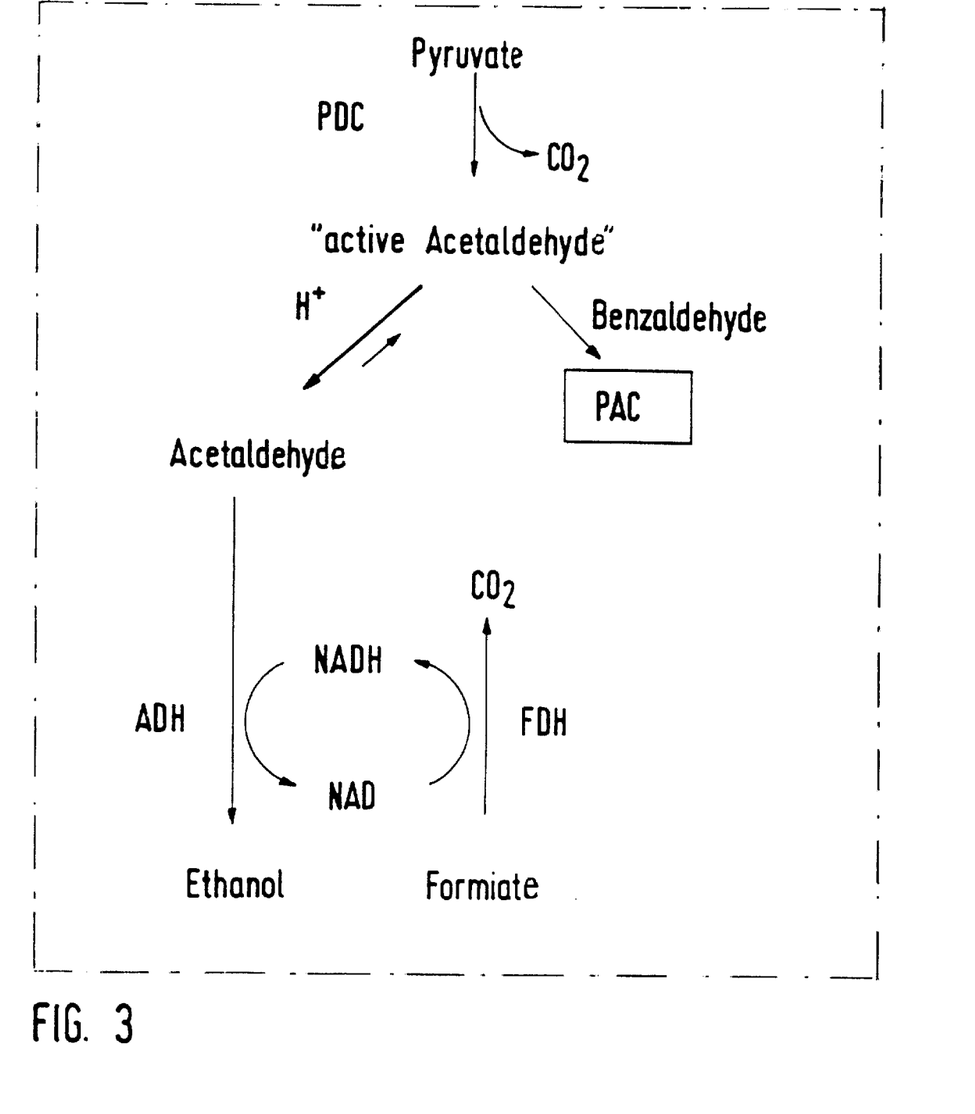
FIG. 3: A scheme for a production of PAC according to FIG. 1 optimized by the interception of acetaldehyde by means of alcohol dehydrogenase.

The enzymatic conversion occurred in accordance with FIG. 3. The use of the alcohol-dehydrogenase (ADH) from yeast (E.C. 1.2.1.2) provides for the regeneration of NADH. The enzymatic PAC synthesis was performed in 20ml Mes/KOH buffer, 50 mM, pH 6.5, mM MgSO$_4$, 1.5 mM ThDP.

The preparation contained:

1.3 U/ml PDC-W392A, 2 U/ml ADH, 2.5 U/ml FDH. The initial pyruvate concentration was 70 mM. In addition, the preparation contained 2 mM NADH and 200 mM formiate. After 120 minutes further 0.7 ml of a 2.1 M pyruvate solution and 0.125 ml of an 8 M sodium formiate solution were added. The pH increase resulting from the enzymatic conversion was counteracted by titration with formic acid. After 7 hours, 6.8 mM PAC had been formed.

Processing and Analysis of the Enzymatic Reaction Products

The reaction products were separated by preparative reversed-phase HPLC. As stationary phase a C8-MOS Hypersil column, 250×4.6 mm was used. The elution occurred under isocratic conditions with acetic acid/acetronitrile 0.5%/12.5% (v/v) with a flow rate of 1.5 ml/min. The elution times under these conditions were: PAC, 4.77 min and 2-hydroxypropiophenon, 5.41 min. The correlation of the generated enantiomers as R-(−)-PAC occurred by means of polarimetry on the basis of a standard from the PAC production (Knoll AG).

The enantiomere ratio of PAC was determined by means of chiral gas chromatography at >>98%.

What is claimed is:

1. A process for producing a pyruvate decarboxylase (PDC) with a specific activity with respect to phenylacetyl carbinol formation of >1 U/mg wherein the PDC produces (R)-(−)-phenylacetyl carbinol (I) in >95% enantiomeric purity with a product ratio of I to 2-hydroxypropiophenon of >95%, comprising isolation from a producer organism, wherein the producer organism comprises a gene of *Zymomonas mobilis* coding for PDC, and further comprising replacement of the TGG codon at position 1174–1176, coding for tryptophan, by a codon which codes for an amino acid residue with a reduced volume ratio.

2. A process according to claim 1, wherein the codon TGG is replaced by a codon which codes for a simple amino acid residue.

3. A process according to claim 2, wherein the codon TGG is replaced by a codon which codes for an aliphatic amino acid residue.

4. A process according to claim 3, wherein the codon TGG is replaced by a codon which codes for an alanine residue.

5. A pyruvate-decarboxylase capable of converting pyruvate in the presence of benzaldehyde into (R)-(−)-phenyl acetylcarbinol in >95% enantiomere purity with a product ratio of I to 2-hydroxypropiophenon of >95% with a specific activity with respect to the product formation of >1 U/mg obtained in accordance with claim 1 the tryptophan residue of which is replaced in the position 397 by an amino acid residue of lesser size.

6. A pyruvate decarboxylase according to claim 5, characterized by an alanine residue replacing the tryptophan residue at the position 392.

7. A process for the enzymatic production of acyloines by enzymatic acyloine-condensation of at least one of an α-keto-carbon acid and aldehydes in the presence of PDC, wherein an enzyme according to claim 5 is used.

8. A process according to claim 7, wherein the acyloinic condensation is performed by alcohol dehydrogenase and NADH starting with an α-ketocarbon acid with concurrent reduction of excess aldehyde formed by decarboxylization.

9. A process according to claim 8, characterized in that the NAD formed during the conversion is regenerated in situ to NADH by formiate-dehydrogenase.

10. A DNA sequence of the gene for a thiamindiphosphate dependent enzyme with an access limitation in the substrate canal leading to the active center, wherein, in place of the codon coding for the access limitation, a codon is introduced which codes for an amino acid residue which eliminates the access limitation.

11. A DNA sequence according to claim 10, wherein the DNA sequence is the pyruvate decarboxylase of *Zymomonas mobilis* wherein the codon at the position 1174–1176 is replaced with a codon which codes for an amino acid residue of lesser size.

12. A DNA sequence according to claim 11, wherein a codon at the position 1174–1176 which codes for a residue of an aliphatic amino acid.

13. A DNA sequence according to claim 12, wherein a codon at the position 1174–1176 codes for an alanine residue.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 1707 BASE PAIRS
      (B) TYPE: NUCLEIC ACID
      (C) STRANDEDNESS: DOUBLE
      (D) TOPOLOGY: CIRCULAR    (ii) MOLECULE TYPE: DNA-Sequence of wild-type pyruvate decarboxylase
        from Zymomonas mobilis    (xi) SEQUENCE DESCRIPTION: SEQ NO:1:

```
ATGAGTTATA CTGTCGGTAC CTATTTAGCG GAGCGGCTTG TCCAGATTGG      50

TCTCAAGCAT CACTTCGCAG TCGCGGGCGA CTACAACCTC GTCCTTCTTG     100

ACAACCTGCT TTTGAACAAA AACATGGAGC AGGTTTATTG CTGTAACGAA     150

CTGAACTGCG GTTTCAGTGC AGAAGGTTAT GCTCGTGCCA AAGGCGCAGC     200

AGCAGCCGTC GTTACCTACA GCGTTGGTGC GCTTTCCGCA TTTGATGCTA     250

TCGGTGGCGC CTATGCAGAA AACCTTCCGG TTATCCTGAT CTCCGGTGCT     300

CCGAACAACA ACGACCACGC TGCTGGTCAT GTGTTGCATC ACGCTCTTGG     350

CAAAACCGAC TATCACTATC AGTTGGAAAT GGCCAAGAAC ATCACGGCCG     400

CCGCTGAAGC GATTTACACC CCGGAAGAAG CTCCGGCTAA AATCGATCAC     450

GTGATCAAAA CTGCTCTTCG CGAGAAGAAG CCGGTTTATC TCGAAATCGC     500

TTGCAACATT GCTTCCATGC CCTGCGCCGC TCCTGGACCG GCAAGTGCAT     550

TGTTCAATGA CGAAGCCAGC GACGAAGCAT CCTTGAATGC AGCGGTTGAC     600

GAAACCCTGA AATTCATCGC CAACCGCGAC AAAGTTGCCG TCCTCGTCGG     650
```

```
            CAGCAAGCTG  CGCGCTGCTG  GTGCTGAAGA  AGCTGCTGTT  AAATTCACCG    700

ACGCTTTGGG  CGGTGCAGTG  GCTACTATGG  CTGCTGCCAA  GAGCTTCTTC    750

CCAGAAGAAA  ATGCCAATTA  CATTGGTACC  TCATGGGGCG  AAGTCAGCTA    800

TCCGGGCGTT  GAAAAGACGA  TGAAAGAAGC  CGATGCGGTT  ATCGCTCTGG    850

CTCCTGTCTT  CAACGACTAC  TCCACCACTG  GTTGGACGGA  TATCCCTGAT    900

CCTAAGAAAC  TGGTTCTCGC  TGAACCGCGT  TCTGTCGTTG  TCAACGGCAT    950

TCGCTTCCCC  AGCGTTCATC  TGAAAGACTA  TCTGACCCGT  TTGGCTCAGA   1000

AAGTTTCCAA  GAAAACCGGT  TCTTTGGACT  TCTTCAAATC  CCTCAATGCA   1050

GGTGAACTGA  AGAAAGCCGC  TCCGGCTGAT  CCGAGTGCTC  CGTTGGTCAA   1100

CGCAGAAATC  GCCCGTCAGG  TCGAAGCTCT  TCTGACCCCG  AACACGACGG   1150

TTATTGCTGA  AACCGGTGAC  TCTTGGTTCA  ATGCTCAGCG  CATGAAGCTC   1200

CCGAACGGTG  CTCGCGTTGA  ATATGAAATG  CAGTGGGGTC  ACATTGGTTG   1250

GTCCGTTCCT  GCCGCCTTCG  GTTATGCCGT  CGGTGCTCCG  GAACGTCGCA   1300

ACATCCTCAT  GGTTGGTGAT  GGTTCCTTCC  AGCTGACGGC  TCAGGAAGTT   1350

GCTCAGATGG  TTCGCCTGAA  ACTGCCGGTT  ATCATCTTCT  TGATCAATAA   1400

CTATGGTTAC  ACCATCGAAG  TTATGATCCA  TGATGGTCCG  TACAACAACA   1450

TCAAGAACTG  GGATTATGCC  GGTCTGATGG  AAGTGTTCAA  CGGTAACGGT   1500

GGTTATGACA  GCGGTGCTGC  TAAAGGCCTG  AAGGCTAAAA  CCGGTGGCGA   1550

ACTGGCAGAA  GCTATCAAGG  TTGCTCTGGC  AAACACCGAC  GGCCCAACCC   1600

TGATCGAATG  CTTCATCGGT  CGTGAAGACT  GCACTGAAGA  ATTGGTCAAA   1650

TGGGGTAAGC  GCGTTGCTGC  CGCCAACAGC  CGTAAGCCTG  TTAACAAGCT   1700

CCTCTAG                                                      1707
```